(12) United States Patent
Eriksson et al.

(10) Patent No.: US 9,693,908 B2
(45) Date of Patent: Jul. 4, 2017

(54) WOUND TREATMENT DEVICE EMPLOYING NEGATIVE PRESSURE

(71) Applicant: APPLIED TISSUE TECHNOLOGIES LLC, Newton, MA (US)

(72) Inventors: Elof Eriksson, Wellesley Hills, MA (US); Michael Broomhead, Scituate, MA (US)

(73) Assignee: APPLIED TISSUE TECHNOLOGIES LLC, Hingham, MA (US)

( * ) Notice: Subject to any disclaimer, the term of this patent is extended or adjusted under 35 U.S.C. 154(b) by 211 days.

(21) Appl. No.: 14/530,107

(22) Filed: Oct. 31, 2014

(65) Prior Publication Data

US 2015/0119857 A1  Apr. 30, 2015

Related U.S. Application Data

(63) Continuation-in-part of application No. 14/092,004, filed on Nov. 27, 2013, which is a continuation of (Continued)

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61M 1/0003* (2013.01);
(Continued)

(58) Field of Classification Search
CPC ............. A61M 1/0072; A61M 1/0088; A61F 13/0216; A61F 13/00068
See application file for complete search history.

(56) References Cited

U.S. PATENT DOCUMENTS 2,283,089 A    5/1942  Pfauser
4,469,092 A *  9/1984  Marshall ............... A61H 7/006
                                            601/136
(Continued)

FOREIGN PATENT DOCUMENTS

CN    1420792    5/2003
CN    1571682    1/2005
(Continued)

OTHER PUBLICATIONS

Gross, Lisa. "Face of Hope." Discover: Science for the Curious. Sep. 2014, pp. 44-53.

*Primary Examiner* — Tatyana Zalukaeva
*Assistant Examiner* — Benjamin Klein
(74) *Attorney, Agent, or Firm* — Lando & Anastasi, LLP

(57) ABSTRACT

Devices and methods for wound treatment are disclosed. A chamber may define a treatment space having an interior engineered surface including a plurality of structures configured to provide pathways for the distribution of negative pressure and to exert mechanical stress on a wound. In some specific embodiments, the devices and methods may treat wounds on the head, neck, and face. One or more tubes may be in fluid communication with the treatment space to facilitate the application of negative pressure, the introduction of therapeutic agents, and the removal of wound material.

17 Claims, 15 Drawing Sheets

Related U.S. Application Data application No. 12/601,394, filed as application No. PCT/US2008/064897 on May 27, 2008, now Pat. No. 8,632,523.

(60) Provisional application No. 60/931,599, filed on May 24, 2007.

(52) U.S. Cl.
CPC ........ *A61M 1/0011* (2013.01); *A61M 1/0072* (2014.02); *A61M 1/0088* (2013.01); *A61M 1/0025* (2014.02); *A61M 1/0084* (2013.01)

(56) References Cited

U.S. PATENT DOCUMENTS

| | | |
|---|---|---|
| 5,034,006 A | 7/1991 | Hosoda et al. |
| 5,312,385 A | 5/1994 | Greco |
| 5,437,602 A | 8/1995 | Polyakov et al. |
| 5,437,651 A | 8/1995 | Todd et al. |
| 5,447,504 A | 9/1995 | Baker et al. |
| 5,527,265 A | 6/1996 | McKeel |
| 5,720,713 A | 2/1998 | Hutchison |
| 5,807,290 A | 9/1998 | Barry |
| 6,053,882 A | 4/2000 | Johansen |
| 6,290,685 B1 | 9/2001 | Insley et al. |
| 6,345,623 B1 | 2/2002 | Heaton et al. |
| 6,566,577 B1 | 5/2003 | Addison et al. |
| 6,652,484 B1 | 11/2003 | Hunckler et al. |
| 6,855,135 B2 | 2/2005 | Lockwood et al. |
| 7,128,735 B2 | 10/2006 | Weston |
| 7,216,651 B2 | 5/2007 | Argenta et al. |
| 7,276,051 B1 | 10/2007 | Henley et al. |
| 7,867,206 B2 | 1/2011 | Lockwood et al. |
| 7,884,258 B2 | 2/2011 | Boehringer et al. |
| 2002/0065494 A1 | 5/2002 | Lockwood et al. |
| 2002/0161317 A1 | 10/2002 | Risk et al. |
| 2002/0198503 A1 | 12/2002 | Risk et al. |
| 2004/0064111 A1 | 4/2004 | Lockwood et al. |
| 2004/0064132 A1 | 4/2004 | Boehringer et al. |
| 2005/0004534 A1 | 1/2005 | Lockwood et al. |
| 2005/0137539 A1 | 6/2005 | Biggie et al. |
| 2005/0222527 A1 | 10/2005 | Miller et al. |
| 2005/0267424 A1 | 12/2005 | Eriksson et al. |
| 2005/0283105 A1 * | 12/2005 | Heaton ................ A61F 13/023 602/40 |
| 2008/0108977 A1 | 5/2008 | Heaton et al. |
| 2009/0124987 A1 * | 5/2009 | Eriksson ........... A61F 13/00068 604/304 |
| 2009/0312723 A1 | 12/2009 | Blott et al. |

FOREIGN PATENT DOCUMENTS

| | | |
|---|---|---|
| EP | 1310267 A2 | 5/2003 |
| GB | 2378392 A | 2/2003 |
| JP | 51-22888 B2 | 1/2013 |
| WO | 91/08793 | 6/1991 |
| WO | 96/35401 | 11/1996 |
| WO | 99/13793 | 3/1999 |
| WO | 99/65542 A1 | 12/1999 |
| WO | 00/56256 A1 | 9/2000 |
| WO | 01/37922 A2 | 5/2001 |
| WO | 2005/046760 | 5/2005 |
| WO | 2005115523 A1 | 12/2005 |
| WO | 2006114648 A2 | 11/2006 |
| WO | 2007002835 A2 | 1/2007 |

* cited by examiner

WOUND TREATMENT DEVICE
EMPLOYING NEGATIVE PRESSURE

CROSS-REFERENCE TO RELATED APPLICATIONS

This application is a continuation-in-part of U.S. patent application Ser. No. 14/092,004 titled "Wound Treatment Device Employing Negative Pressure" filed on Nov. 27, 2013, which in turn is a continuation of U.S. patent application Ser. No. 12/601,394, now U.S. Pat. No. 8,632,523, titled "Wound Treatment Device Employing Negative Pressure" filed on Sep. 20, 2010, which is a U.S. national stage application under 35 U.S.C. §371 of International Patent Application Serial No. PCT/US2008/064897 filed May 27, 2008, which claims the benefit of priority to U.S. Provisional Patent Application Ser. No. 60/931,599 titled "Wound Treatment Device Employing Negative Pressure" filed May 24, 2007, the entire disclosure of each of which is hereby incorporated herein by reference in its entirety for all purposes.

FIELD OF THE TECHNOLOGY

The disclosure relates generally to wound treatment and, more particularly, to devices for treating wounds with negative pressure and/or therapeutic agents.

BACKGROUND

Many wounds can be treated by the application of negative pressure. The method of such treatment has been practiced for many years. The benefits of such treatment can include: reduction of edema; reduction of wound exudate; reduction of wound size; and stimulation of formation of granulation tissue. Existing devices and appliances for the provision of negative pressure wound therapy are complex. Such devices typically encompass a porous insert such as foam or gauze that is placed into the wound; a tube connecting the inner space to a source of suction; a flexible cover draped over these components and sealed to the skin around the wound; an electrically powered suction pump; controls to operate the pump and monitor the system; containers to collect wound fluids; filters to process the materials removed from the wound; and safety systems to prevent harm to the patient and to block the escape of biological materials into the outside environment. These devices are expensive, labor intensive, and restrictive of patient mobility. These devices are generally not considered suitable for wounds on certain areas of the body, including wounds on the face, neck, and head. The many components, particularly the seals around the insert and the tube, tend to leak. Therefore, suction must be applied either continuously or frequently.

Continuous suction is typically achieved by a vacuum pump powered by an electric motor. Such systems require complex means to measure, monitor, and control the operation of the pump to ensure the safety of the patient. In addition, many negative pressure devices are contraindicated in the presence of necrotic tissue, invasive infection, active bleeding, and exposed blood vessels. They require the use of a porous insert (sponge, foam, gauze, mesh, etc.) in the wound. The insert may present two problems: growth of tissue into the insert, and the harboring of infectious and/or undesirable materials in the insert. Wound tissue can grow into and around such inserts, thereby causing adverse results to the healing process. Moreover, such inserts can retain wound fluid and microorganisms, and therefore can become contaminated and/or infected, presenting an adverse effect to the healing process. In addition, the high cost of these devices may deter or delay their use on patients.

Existing negative pressure treatment devices are labor intensive since they require the user to assemble, fit, and customize a number of components. First, the user must prepare, trim, and size an insert of foam, gauze, mesh, or other material that will be placed in the wound. Next, the user must position a tube in the insert, and then cover the tube and insert with a material that is intended to create a leakproof seal. In practice, and as mentioned above, such compositions tend to leak, requiring the frequent application of suction in order to establish and re-establish negative pressure within the space about the wound. In addition, currently available negative pressure devices and systems block the view of the wound, making monitoring and diagnosis more difficult. This is particularly problematic for wounds on the head, neck and face, such that existing negative pressure devices are not suitable for such wound treatment. Therefore, an improved device for applying negative pressure to wounds is needed.

SUMMARY

In accordance with one or more embodiments, devices and methods for treating wounds with negative pressure and/or therapeutic agents are disclosed.

In some embodiments, a device for wound treatment may have a chamber that includes an inner surface and a sealing portion that defines an isolated treatment space, a plurality of embossed structures arranged in a pattern on the inner surface of the chamber, the structures having a height of about 0.2 mm to about 5 mm and spaced about 0.2 mm to about 10 mm from one another, the structures configured to directly contact a wound and to create pathways for distributing negative pressure between the inner surface of the chamber and the wound, and at least one tube having a first end connected to the chamber, the at least one tube being in fluid communication with the isolated treatment space so as to enable at least one selected from the group of applying negative pressure to the isolated treatment space and applying a therapeutic agent to the wound.

In other embodiments, a wound treatment device may include a chamber configured to enclose a head and neck region of a patient, the chamber being made of an impermeable material that is sufficiently thin to conform to the head and neck of the patient, the chamber having a sealing portion at a base and an interior surface defining an isolated treatment space, a plurality of embossed structures on the interior surface of the chamber, the structures being configured to directly contact a wound and to create pathways for distributing negative pressure between the inner surface of the chamber and the wound, and at least one tube connected to the chamber and in fluid communication with the isolated treatment space so as to enable at least one selected from the group of applying negative pressure to the treatment space and applying a therapeutic agent to the wound.

In at least some embodiments, a method of treating a patient having a facial wound may involve debriding the facial wound, fitting a wound treatment device as described herein over a head of the patient, applying at least one therapeutic agent to the wound via the device at a concentration of up to or greater than about 1000 times a concentration suitable for intravenous delivery, and applying negative pressure wound therapy to the treatment space of the device for a sufficient duration to effect healing of the wound.

In one aspect, the present disclosure is summarized as a device for wound treatment, comprising a chamber that includes an inner surface and defines a treatment space, the chamber being made of a flexible, impermeable material. The device further includes a plurality of structures configured to exert mechanical stress on a wound and configured to create pathways through which negative pressure can be distributed and maintained in the treatment space, the plurality of structures intruding from the inner surface of the chamber into the treatment space. The device further includes a tube having a first end connected to the chamber, the tube being in fluid communication with the treatment space so as to enable at least one selected from the group of applying negative pressure to the treatment space and applying a therapeutic agent.

In some embodiments, the plurality of structures and the chamber are part of a single ply of material. In addition, in some embodiments, each of the structures in the plurality of structures is semi-rigid.

In some embodiments, the device includes a wedge-shaped manual pump, and the treatment space is in fluid communication with the wedge-shaped manual pump. The wedge-shaped manual pump may include a spring that biases the wedge-shaped manual pump to an uncompressed position.

The foregoing and other objects and advantages of the disclosure will appear in the detailed description that follows. In the description, reference is made to the accompanying drawings that illustrate a non-limiting preferred embodiment of the invention.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention and are not intended as a definition of the limits of the invention. For purposes of clarity, not every component may be labeled in every drawing. In the following description, various embodiments of the present invention are described with reference to the following drawings, in which.

Figure 1:
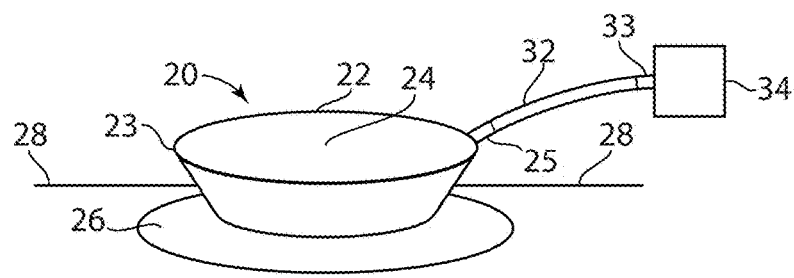
FIG. 1 is a perspective view of a wound chamber treatment device with a tube leading from a chamber to a suction source.

While the invention is susceptible to various modifications and alternative forms, specific embodiments thereof have been shown by way of example in the drawings and are described below in detail. It should be understood, however, that the description of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The present disclosure is directed to providing a simple, safe, disposable, and cost-effective device that is easy to install and operate, that allows freedom of motion to the patient, and that overcomes, or at least reduces the effects of, one or more of the problems set forth above. In at least some embodiments, the present disclosure does not require the use of an interface layer such as a porous insert. In some embodiments, a one-piece, two-piece, or multi-piece construction of the device is suitable for patient treatment and eliminates virtually all leaks, therefore preserving and maintaining negative pressure within the wound without the need for constant or frequent regeneration of negative pressure. In addition, the structure of the device is configured to promote wound healing and to create pathways through which negative pressure can be distributed and maintained in the treatment space. The device may contact the wound directly, without the use of an interface layer such as a porous insert. The indications for the present disclosure may be expanded beyond the limitations imposed on current devices. The cost-effectiveness of the present disclosure may lead to the provision of negative pressure wound therapy on a more widespread basis and earlier in the timeline of wound care.

In accordance with various aspects and embodiments, the devices and methods of the present disclosure may be used to treat full and partial thickness burns, traumatic wounds, post surgical wounds, infected wounds, post infection wounds, skin loss due to dermatological conditions, and other conditions that result in skin and deep tissue loss. The devices and methods may be used anywhere on the human body, and may also be suitable for veterinary applications. The devices and methods may, for example, be used for wound preparation to prevent scarring as well as the fixation and protection of skin grafts during wound treatment. In some specific non-limiting embodiments discussed herein, wound treatment may relate to injuries occurring on the head, face, and/or neck. For example, a patient's cheeks, forehead, and/or crown may be treated. The head including facial tissue presents unique challenges which may be addressed in accordance with one or more embodiments.

One aspect of the present disclosure is seen in a wound treatment device including a chamber defining a treatment space around the wound. The flexible adhesive base of the chamber forms a water-tight and gas-tight seal. A tube communicates from the treatment space to a source of suction. In at least some embodiments described herein, the source of suction is capable of generating and/or maintaining sub-atmospheric pressure within an enclosed space. The suction source also serves as a receptacle for materials removed from the chamber, including wound fluid. All components preferably are inexpensive, lightweight, and disposable.

Figure 2:
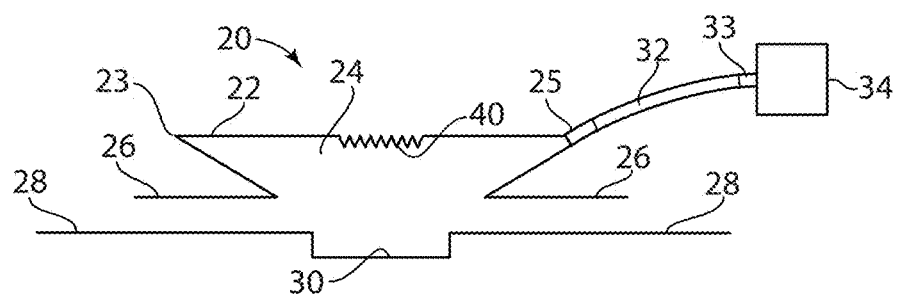
FIG. 2 is a side sectional view of the device in FIG. 1.
Figure 19:
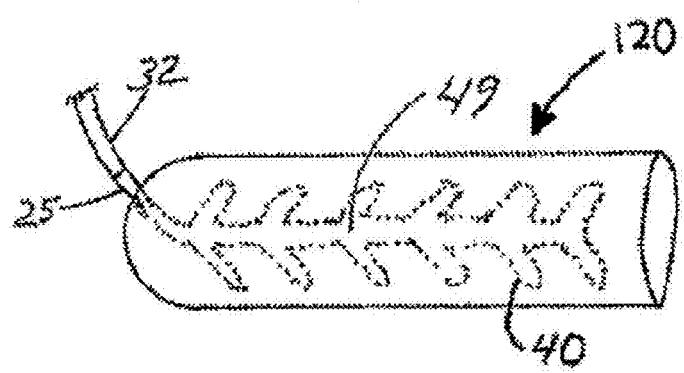
FIG. 19 is a view of a wound chamber configured as a tube for placement over a limb, and having engineered structures and channels on the interior surface of the chamber wall.
Figure 26:
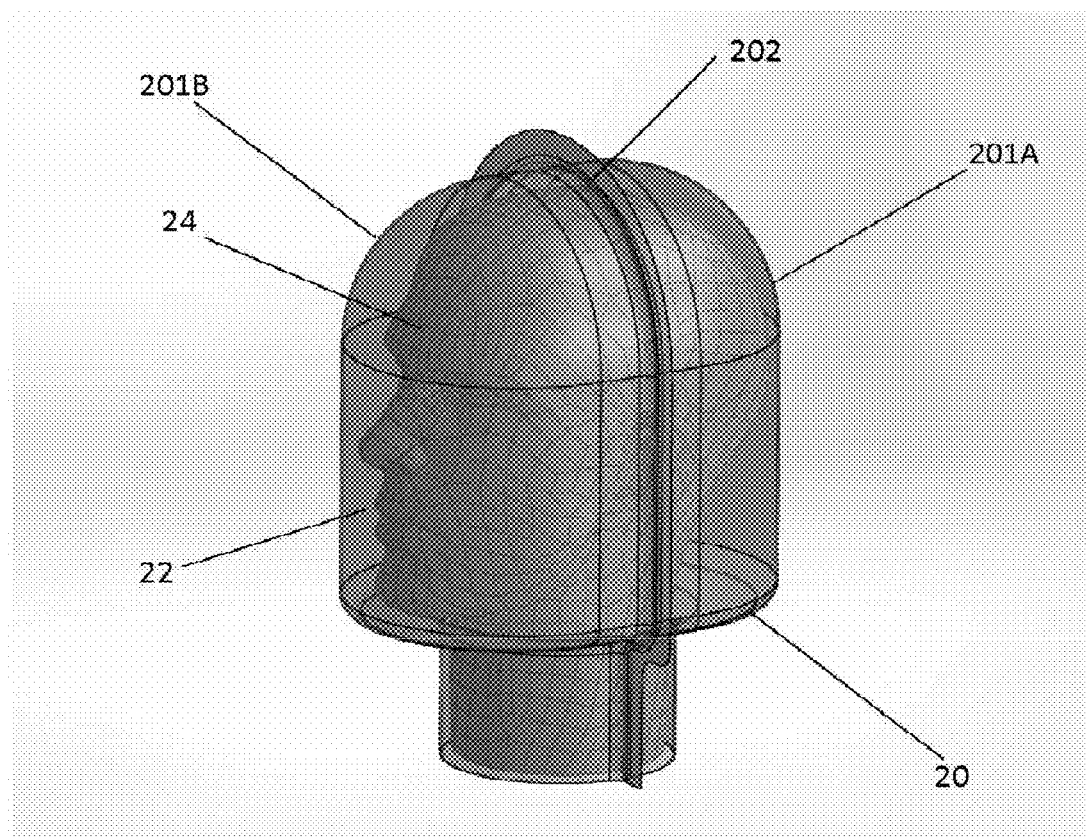
FIG. 26 is a perspective view of a wound chamber treatment device for wounds on the face, head, and neck in accordance with one or more embodiments.

Referring to FIGS. 1 and 2, views of a wound treatment device 20 are provided. The device 20 includes a chamber 22 defining a treatment space 24 and a base 26 that may be sealed to a skin surface 28 of a patient over a wound 30. In the illustrated embodiment, the chamber 22 has a bellows configuration with a fold 23. However, the invention is not no limited, and other configurations of a chamber formed of a flexible, moisture and gas impermeable material may be used. The chamber may also be transparent to allow for visual inspection of the wound during treatment. In accordance with certain embodiments, the material is substantially transparent. In other embodiments, the material may be substantially opaque. The use of an impermeable material is particularly advantageous for introducing therapeutic agents to the wound. Additionally, the impermeable nature of the chamber material prevents water loss from the wound, which facilitates improved healing. Materials from which the device 20 may be made will be discussed in further detail below. The device 20 can be designed for use with any wound on any body part, including both human and veterinary applications. Various geometries such as circular, square, rectangular, tubular, pouch, envelope or other shapes may be implemented based on the intended application. In accordance with some embodiments, chamber 22 defining treatment space 24 may be configured for a specific body part. For example, a chamber in the form of a tube or sleeve for placement over a limb is shown in FIG. 19, whereas a chamber in the form of a hood for placement over a head is shown in FIG. 26 as described further below.

Still referring to FIGS. 1 and 2, a dermal or cutaneous adhesive material may be provided on a bottom surface of the base 26 for providing a fluid-tight seal with sufficient adhesive strength to prevent inadvertent removal of the chamber 22 or breach of the fluid-tight seal during normal patient movement. Numerous adhesive materials sufficient for these purposes are known to those of ordinary skill in the art.

Figure 27:
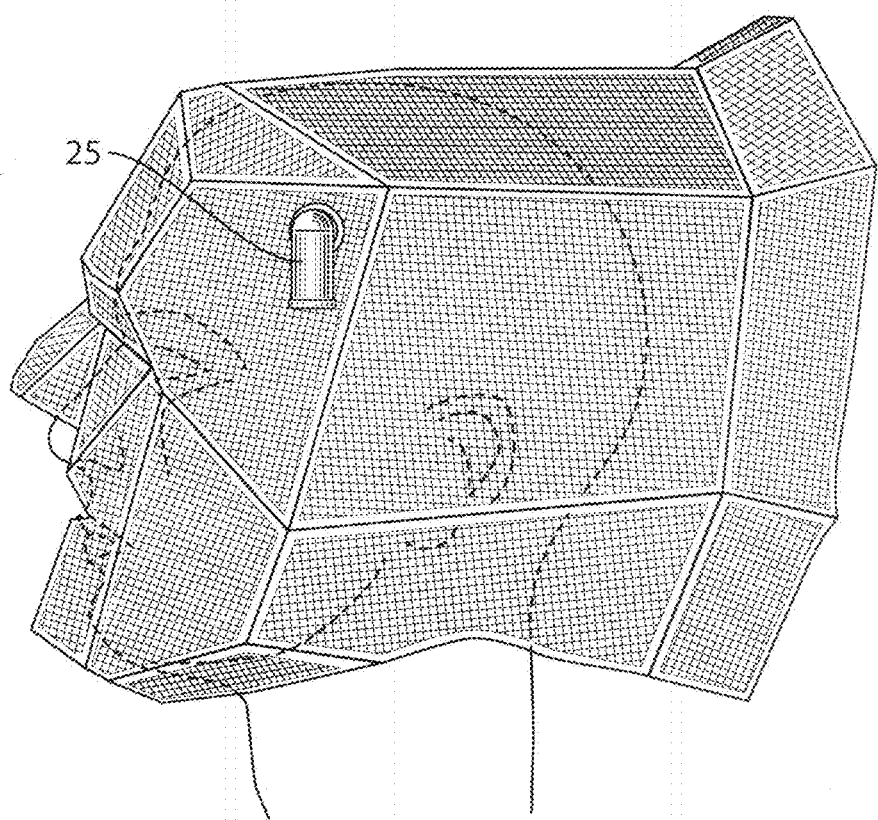
FIG. 27 is a perspective view of another embodiment of a wound chamber treatment device for wounds on the face, head, and neck in accordance with one or more embodiments.

In accordance with some embodiments, device 20 can be specifically designed for treating wounds occurring on the head, face, and/or neck. The device may cover only the head, or both the head and neck. Referring again to FIG. 26, a chamber may be formed that fits over the head and attaches at the base of the neck for example at, or proximate, the collar bone. In some embodiments, the chamber may be defined by a single piece of material, or a two or more piece design may be implemented. The device may be oversized to fit any size head or may be customized. Oversized devices may lead to the presence of wrinkles in use which may be advantageous for negative pressure distribution. In accordance with other embodiments and referring to FIG. 26, the device may be comprised of two pieces 201A and 201B that may adhesively join to form a seam 202, for example, around the midline of the head and across the ears. In some embodiments, the pieces may be joined by other methods, and may for example, by a zipper type or ziploc seal. Still, in accordance with other embodiments and as shown in FIG. 27, the device may be made from a plurality of pieces that contour the face.

Figure 28:
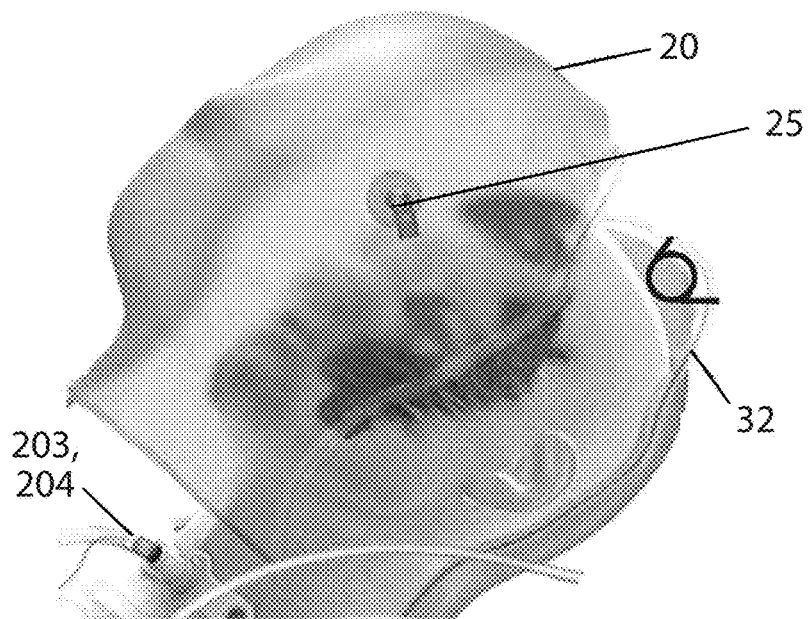
FIG. 28 is a perspective view of an unassembled wound chamber treatment device for wounds on the face, head, and neck in accordance with one or more embodiments.
Figure 29:
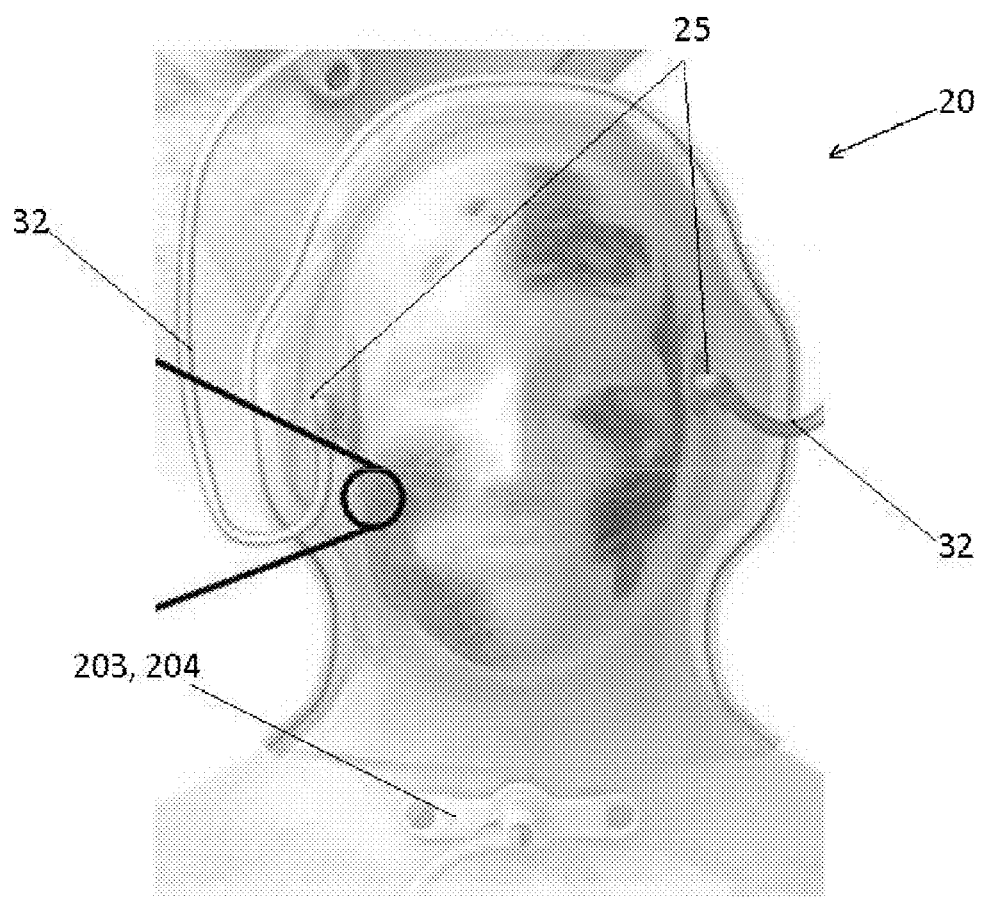
FIG. 29 is a front view of an assembled wound chamber treatment device for wounds on the face, head, and neck in accordance with one or more embodiments.

The head device may or may not have openings for the nose and mouth. If the device is constructed to cover the nose and mouth, the nose and mouth may be surgically sealed for treatment. For example, soft conforming obturators, or alternatively, sutures may be used. Referring to FIG. 28, a patient being treated with a device 20 covering the nose and mouth may breathe via an installed tracheostomy tube 203 and be fed via an installed gastrostomy tube 204. These tubes may be fitted outside of the device, for example, at the neck. Contact lenses (not shown), such as oversized lenses, may be used to protect the eyeballs during treatment.

A tube 32 is attached to the chamber 22 preferably at a location spaced above the base 26 and communicates with the treatment space 24. The tube 32 is constructed to maintain its shape without collapsing and to permit the passage of wound fluids and wound debris. The tube 32 may be permanently fixed to the chamber 22, or a fitting, such as a tubular port 25 may be provided to allow the attachment and removal of the tube 32 or any other device that can deliver material or therapies to, or remove material from, the treatment space 24. The tube 32 may terminate at a wall of the chamber 22, or it may extend through the wall a distance and terminate within the treatment space 24, where it may communicate with such space, with channels formed on the inner surface of the chamber wall, or with folds formed in the chamber wall. The tube 32 is sealed to the chamber 22 in such a manner as to prevent the escape of liquid or gas from the treatment space 24 to the outside environment. A distal end of the tube 32 terminates at a device that generates sub-atmospheric pressure, such as suction device 34. The suction device 34 may be a pump, although other types of devices may be used as discussed below. A fitting 33 may be provided to permit the detachment and reattachment of a suction device 34 to the tube 32.

Referring to FIG. 28, when device 20 is used to treat face, head, and/or neck wounds, the device 20 may comprise a plurality of tubular ports 25 for communication with one or more tubes 32. The ports 25 may be strategically placed based on the geometry of the chamber. At least one tubular port 25 may be located at the top of the device and at least one tubular port 25 may be located at the bottom of the device. In accordance with some embodiments, tubular ports 25 may be positioned on the side of the patient's face, at the temples proximate the ears. In some embodiments, there are at least two tubular ports present.

Figure 3:
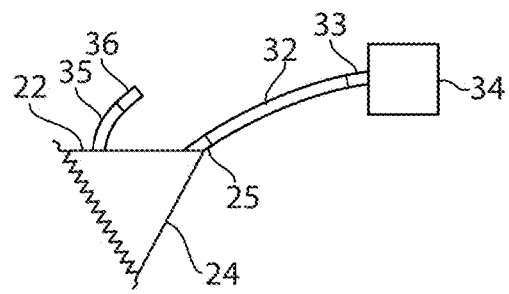
FIG. 3 is a sectional view of the device in FIG. 1 with an additional tube leading to a port.
Figure 4:
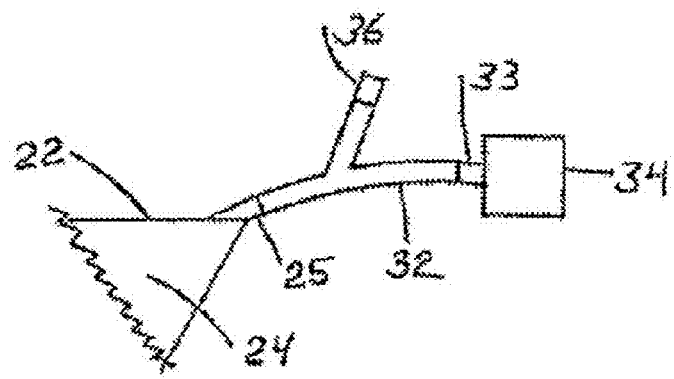
FIG. 4 is a sectional view of the device in FIG. 1 with a branching tube leading to a port.

Turning to FIG. 3, a sectional view of the device 20 is provided, showing a second tube 35 attached to the chamber 22 and communicating with the treatment space 24, with channels, or with folds. A distal end of the tube 35 terminates in a portal 36. The disclosure is not limited to any number of communicating tubes, and multiple tubes and portals may be provided for accessing the treatment space 24. FIG. 4 shows the device in FIG. 1 with a branch of the tube 32 that leads to a portal 36. The portal 36 may be used for the delivery of therapeutic agents—such as antimicrobials, antibiotics, antifungals, and analgesics—prior to, during, or after the delivery of negative pressure. As such, the portal 36 may be a lure configured for attaching to a container or a syringe. Alternatively, therapeutic agents may be delivered through the same tube 32 that communicates with the suction device 34.

In accordance with some embodiments, the device may allow for the delivery of a therapeutic agent directly to the wound. As such, the therapeutic agents can be delivered in concentrations significantly higher than could otherwise be administered intravenously or orally. For example, antibiotics can be applied directly to the wound at concentrations in a range from about the conventional oral concentration to up to about 1000 times the conventional oral concentration, or even higher. If ingested or administered directly to the bloodstream, these concentrations would be toxic to the body. Topical application facilitates the use of significantly higher concentrations that facilitate healing. Combinations of therapeutic agents, such as analgesics, antibiotics, and chemical debriding agents may also be used, and may advantageously reduce or eliminate the need for surgical debridement of the wound.

Figure 5:
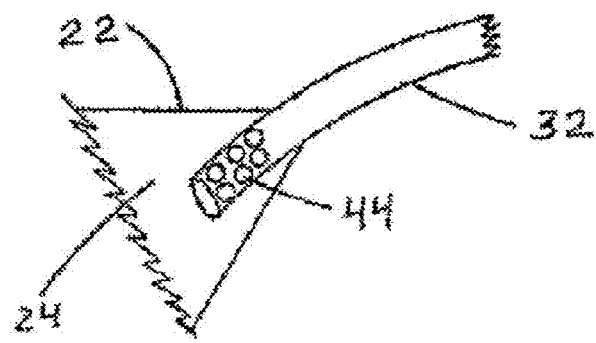
FIG. 5 is a perspective view of the end of the tube communicating with the interior chamber space.

Turning now to FIG. 5, the end of the tube 32 extending into the chamber space 24 is shown with multiple holes 44. The purpose of the holes 44 is to ensure that gases, liquids, wound fluid, debris, and other materials can flow and move out of the chamber space 24 into the tube 32 without impediment.

The wound may advantageously be monitored through the substantially transparent chamber material. The negative pressure device 20 may also be equipped with sensors to monitor certain parameters within the chamber space 24. For example, oxygen, carbon dioxide, pH, temperature, and other parameters may be measured and monitored.

Figure 6:
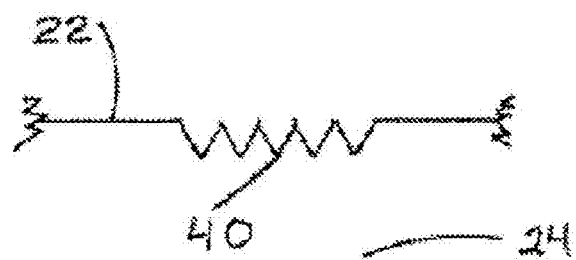
FIG. 6 is a side sectional view of structures engineered on and into the interior surface of the chamber wall, where the structures are of uniform size and shape, and are spaced uniformly apart.
Figure 6A:
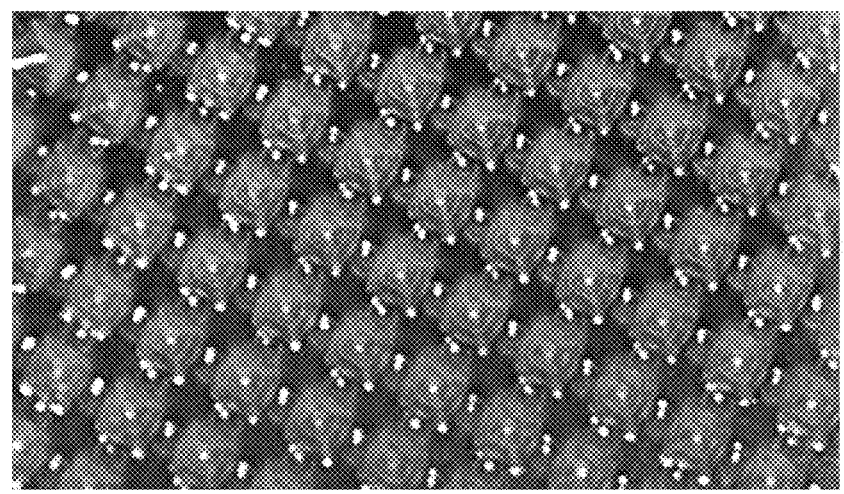
FIGS. 6A-6C present schematics of patterned engineered structures in accordance with one or more embodiments.
Figure 6B:
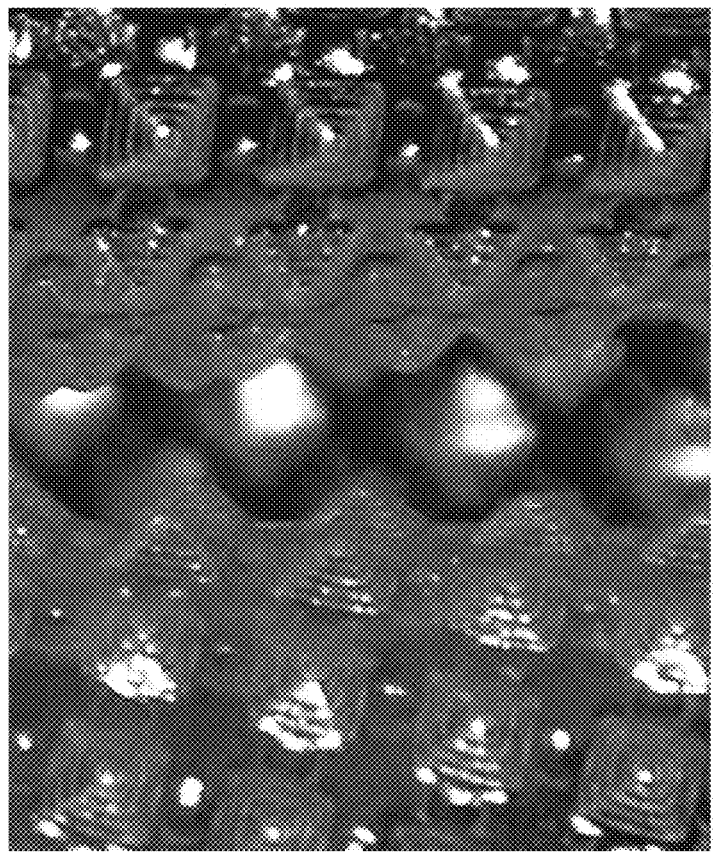
Figure 6C:
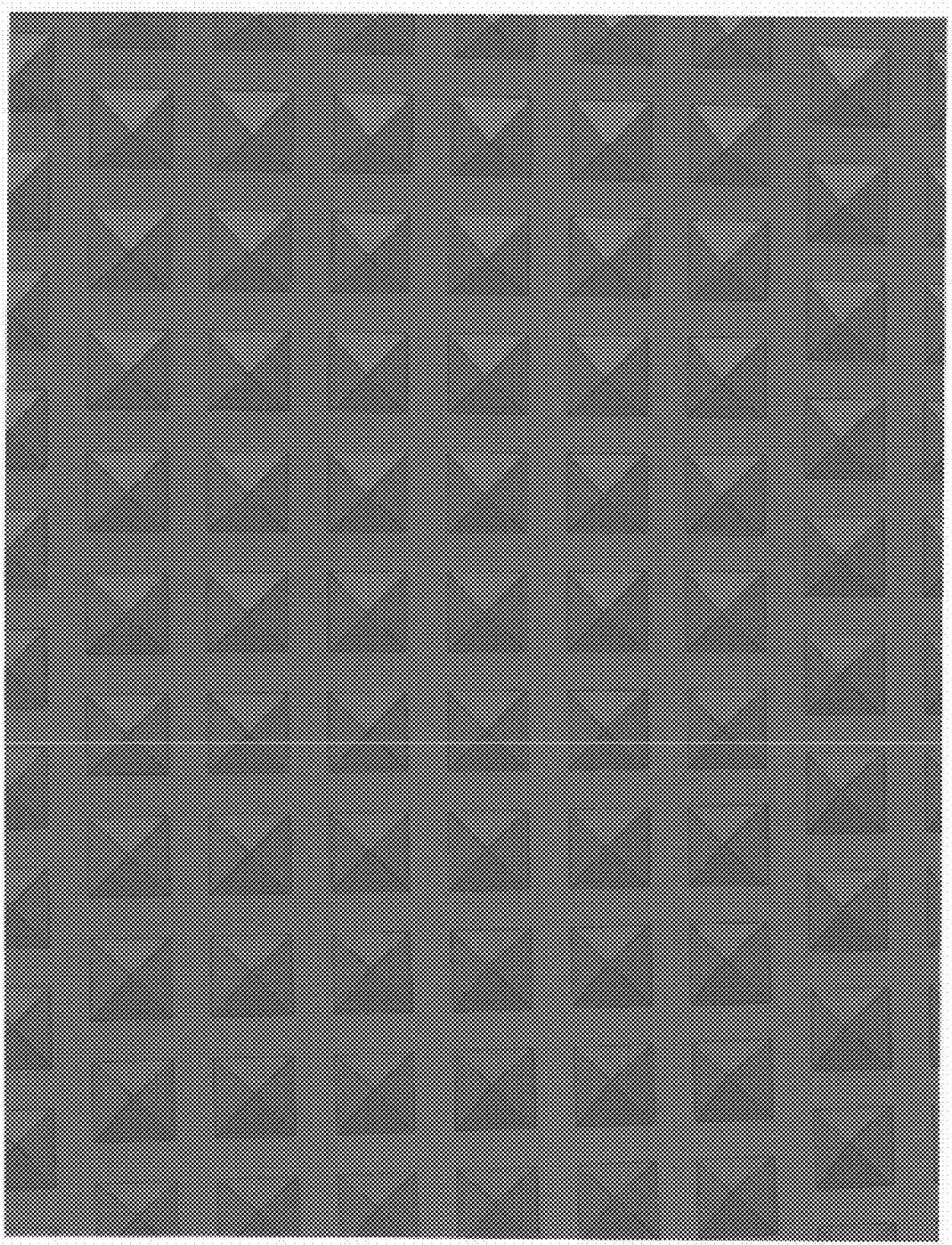

Referring to FIG. 6, the interior surfaces of the chamber wall may be configured with structures 40 that are engineered on the surfaces. FIGS. 6A-6C present schematics of different patterned engineered structures in accordance with one or more non-limiting embodiments. The portions of the interior surfaces with engineered structures 40 may be varied from that shown in the figures, and preferably a high percentage of the interior surfaces include engineered structures 40. The structures preferably cover at least 50% of the interior surfaces, and more preferably at least about 95% of the interior surfaces. These structures are raised when viewed from within the chamber space 24, and they intrude into such space in directions generally perpendicular to the interior surfaces of the chamber space 24. These structures can be any shape, including without limitation a cone, a pyramid, a pentagon, a hexagon, a half sphere, a dome, a rod, an elongated ridge with rounded sides, or an elongated ridge with square sides. The structures can be provided as identical shapes, or in any combination of shapes. The structures can be provided with identical sizes, or in any combination of different sizes. The structures can be provided in a regular or irregular pattern on the surface. The distance of intrusion into the chamber treatment space 24 from the chamber wall by such structures (height of such structures) is preferably between 0.01 mm and 20 mm, preferably between 1 mm and 1 cm, and most preferably about 2 mm. The spacing between such structures is preferably between 0.01 mm and 5 cm, and the spacing for example, is most preferably about 2 mm apart. In some embodiments, about 2 mm high structures are arranged about 2 mm apart. When larger structures are used, the structures may be spaced further apart and when smaller structures are used, the structures may be spaced closer together. For example, a configuration of pyramids of 0.2 mm in height may be spaced about 0.2 mm apart, whereas a configuration of larger pyramids of about 5 mm high may be spaced 10 mm apart.

The engineered structures 40 interface with the wound surface during use of the device 20. The engineered structures may directly contact the wound surface. One purpose of these structures is to ensure that negative pressure established within the chamber space 24 is evenly distributed and maintained throughout such space. As negative pressure is established within the tube that leads to the source of suction or sub-atmospheric pressure, the chamber will lie tighter against the wound tissue. The device 20 includes the engineered structures 40 in order to define pathways to establish, distribute, and maintain negative pressure across the wound surface and prevent complete contact between the inner surfaces of the chamber and the wound tissue. Without such structures, the chamber wall would make complete contact with the wound surface. As a result, there would be no space within which negative pressure could be established, distributed, and maintained. Therefore, the engineered structures are preferably semi-rigid. The term "semi-rigid" should be understood as meaning that deformation only occurs at a microscopic level under operating negative pressures in the range of 0.5-2 psi. Alternatively, the engineered structures may be somewhat flexible depending on the spacing between the structures. In addition, the structures are engineered to reduce the extent to which wound tissue can enter the space between the structures, so that a sufficient amount of open space is maintained. The engineered structures may be strategically patterned on the surface to produce desired negative pressure pathways within the chamber.

An additional purpose of these structures is to serve as a form of stimulation to the wound to produce beneficial results, including without limitation the formation of granulation tissue and an increase of micromechanical forces. Such mechanical forces provide stimulation to a portion of the wound tissue, which has been suggested as a contributing factor to the effectiveness of negative pressure wound therapy. From the above discussion and the figures, it should be understood that the flexible chamber is movable over a range of positions. The range of positions includes a first position, such as the position shown in FIGS. 1 and 2, in which the engineered structures 40 are spaced apart from the opening of the chamber defined by the base 26. The range of positions also includes a second position in which at least some of the engineered structures 40 are positioned in the opening of the chamber. The second position is preferably a position in which the engineered structures 40 engage the wound.

The chamber wall can be formed of any appropriate medical grade material that has the following characteristics: flexibility, conformability, gas impermeability, liquid impermeability, the ability to be formed, tooled, and engineered, and the ability to retain the shape, function, and effectiveness of raised structures under desired ranges of negative pressure. The material should generally deter adhesion and in-growth. The material is preferably transparent to allow visual inspection of the wound during treatment. In addition, the material is preferably hypo-allergenic and provided to a medical facility in a sterile condition. For example, the chamber device may be made of a flexible, conformable material such as polyurethane, polyethylene, or silicone, although other similar materials may also be used. The material may have a thickness in the range of about 5 mm to about 100 mm. In some embodiments, the material may have a thickness of from about 1 mil up to about 100 mil. In some specific embodiments, a 5 mil polyurethane membrane may be used to form the treatment chamber.

The chamber is preferably designed to provide sufficient material to lie against the surface of the wound tissue without special sizing, trimming, or other customizing operations. The chamber may be made from a single ply of material, or may be constructed of multiple layers of material in and on which the structures are engineered. It should be understood that a single ply chamber may be made of multiple sheets of material during manufacturing, but is provided to a medical facility in a state in which the multiple sheets are bonded or otherwise connected to one another. For example, individual three dimensional shapes may be adhered or bonded to the inner surface of the chamber wall during manufacturing to provide the engineered structures. A single ply chamber could also be formed from a single sheet of material that defines both the chamber walls and the engineered structures. For example, the engineered structures may be embossed. Alternatively, a multiple layer chamber is provided to a medical facility in a state in which layers of material are stacked to form the chamber. For example, the layer facing the interior treatment space of the chamber could be a layer containing engineered structures that is bonded onto a generally flat layer of material (or multiple sheets of generally flat layers) by a medical practitioner.

The engineered structures can be made by techniques familiar to those in the art, such as embossing, stamping, molding, forming, or bonding. If the structures are created by embossing their shape into the material, the embossed structures may be left in a concave state relative to the outside of the chamber as shown in FIG. 6. Embossed structures may also be formed on a single ply of material that also forms the walls of the chamber and the base. This may provide a chamber that is relatively flexible with semi-rigid structures on a single ply of material. Alternatively, the cavities may be filled with a suitable material to render the structures solid. As another alternative, solid structures can be affixed to the inner surfaces of the chamber.

Figure 7:
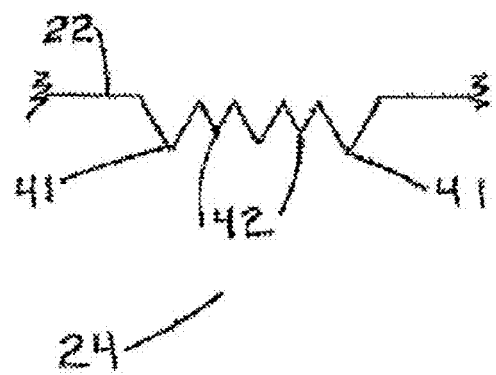
FIG. 7 is a side sectional view of two groups of structures engineered on and into the interior surface of the chamber wall, where one group intrudes into the chamber space, the other group intrudes to a lesser extent, and structures from these groups alternate in a regular pattern.
Figure 8:
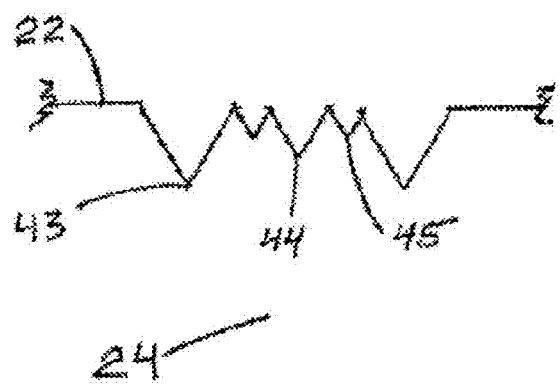
FIG. 8 is a side sectional view of three groups of structures engineered on and into the interior surface of the chamber wall, where such groups have varying degrees of intrusion into the chamber space and alternate in a regular pattern.
Figure 9A:
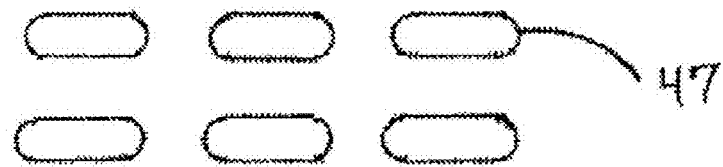
FIG. 9a is an overview of structures engineered on and into the interior surface of the chamber wall, where the structures consist of raised ridges.
Figure 9B:
FIG. 9b is a side sectional view of the raised ridges of FIG. 9a with rounded edges.
Figure 9C:
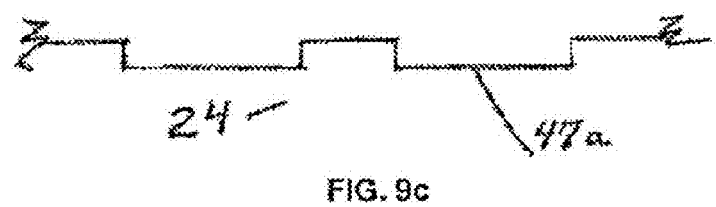
FIG. 9c is a side sectional view of the raised ridges of FIG. 9a with square cross sections.
Figure 10:
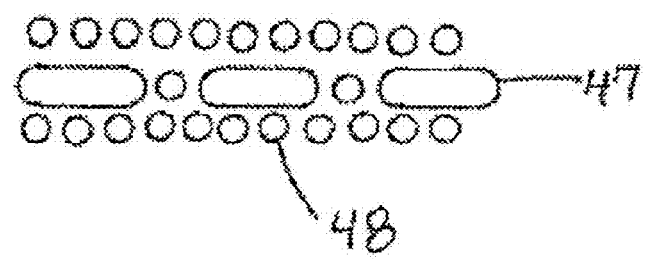
FIG. 10 is an overview of the raised ridge structures shown in FIG. 9a, with the addition of raised dome structures positioned among the ridges.

The raised structures on the inner surfaces of the chamber wall can be configured and distributed in a number of patterns. For example, FIG. 6 is a side sectional view of a portion of a chamber wall, showing engineered structures 40 on the interior surface of the material that faces treatment space 24. Structures 40 are identical in shape and size, and are positioned uniformly apart from one another. As another example, FIG. 7 is a side sectional view showing engineered structures 41 and 42 intruding into the chamber space, where structures 41 intrude farther than structures 42, and the structures are configured in a regular alternating pattern of 41-42-41-42 and so forth. As yet another example, FIG. 8 is a side sectional view showing engineered structures 43, 44, and 45 intruding into the chamber space, where structures 43 intrude farther than structures 44 and 45, structures 44 intrude less than structures 43 but farther than structures 45, and structures 45 intrude less than structures 43 and 44. These structures are configured in a regular alternating pattern of 43-45-44-45-43-45-44-45-43 and so forth. The embodiment shown in FIG. 8 makes it difficult for soft wound tissue to penetrate all of the spaces among the raised structures. A sufficient amount of continuous space is established to make possible the distribution of negative pressure, as well as the addition of fluids and therapies and the removal of fluids and materials from the wound. As yet another example, FIG. 9a is an overview of a portion of the chamber wall, showing engineered structures 47 in the form of raised ridges. The engineered structures 47 may be rounded (FIG. 9b), square (FIG. 9c), or a combination thereof when viewed from the side. As yet another example, FIG. 10 is an overview showing engineered dome structures 48 interspersed with ridge structures 47. The engineered dome structures 48 are preferably semi-spherical when viewed from the side, although other shapes are contemplated.

Figure 11:
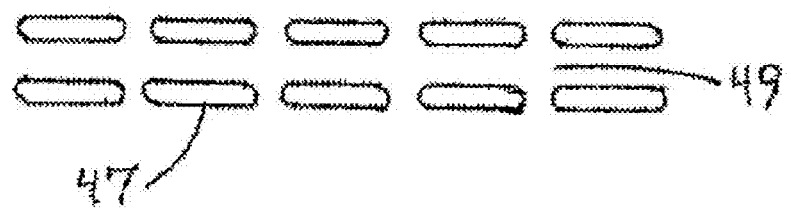
FIG. 11 is an overview of raised ridge structures engineered on and into the interior surface of the chamber wall, where two parallel lines of such structures form a channel.
Figure 12:
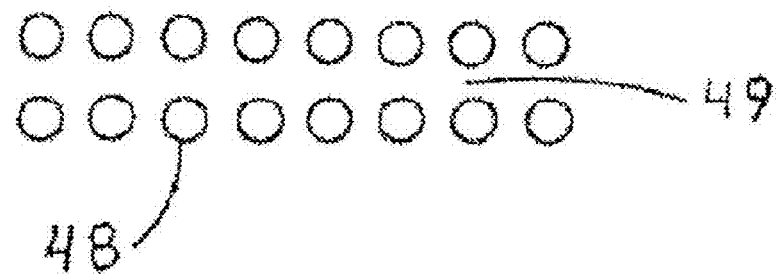
FIG. 12 is an overview of raised dome structures engineered on and into the interior surface of the chamber wall, where two parallel lines of such structures form a channel.
Figure 13:
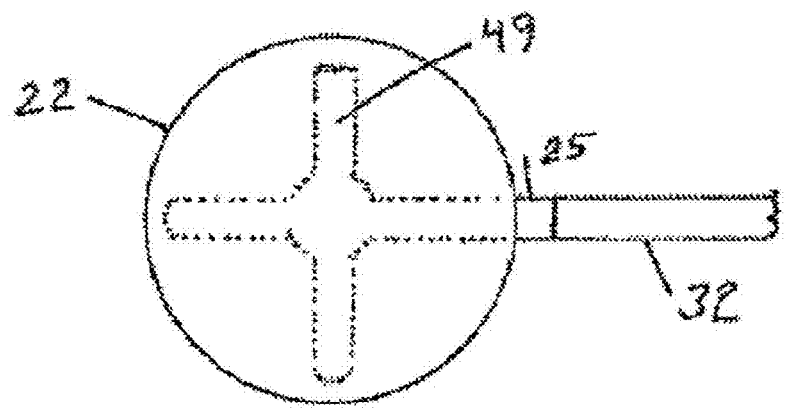
FIG. 13 is a view of a wound chamber, showing a pattern of channels leading to the center of the chamber and then to the tube communicating from the interior of the chamber space.
Figure 14:
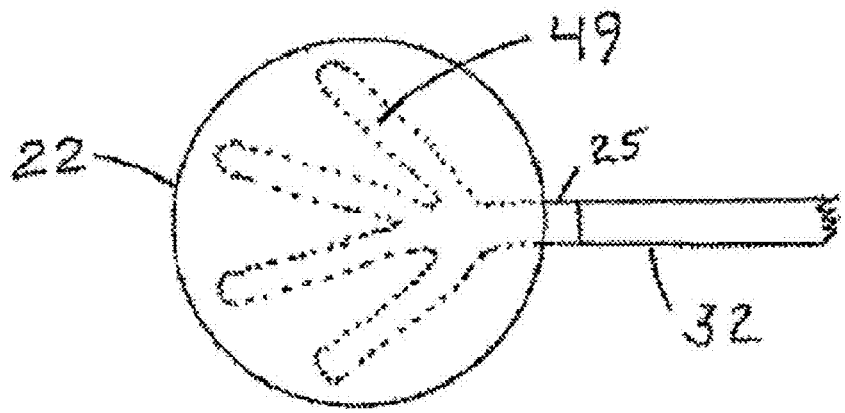
FIG. 14 is a view of a radiating pattern of channels leading to the communicating tube.
Figure 15:
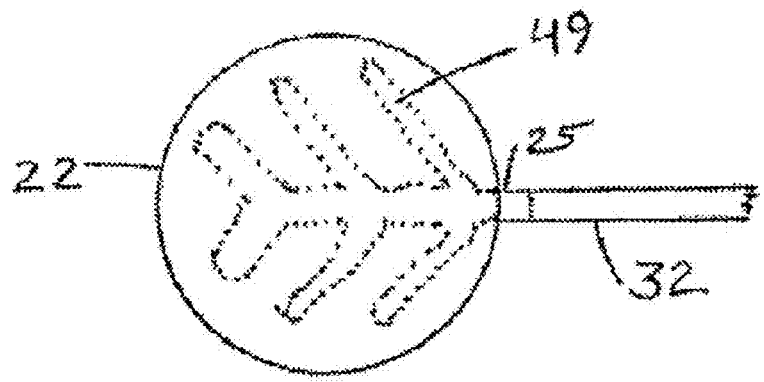
FIG. 15 is a view of a branching pattern of channels leading to the communicating tube.
Figure 16:
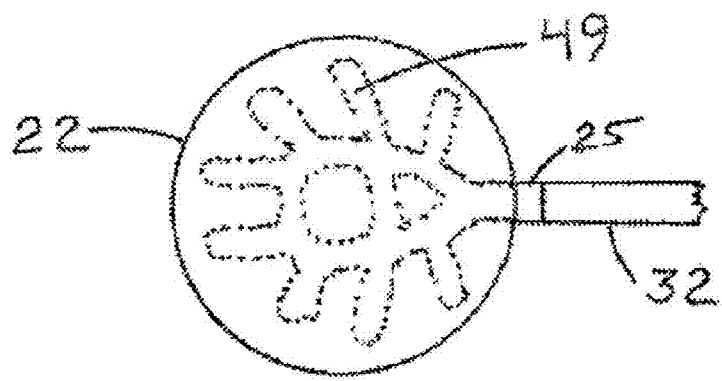
FIG. 16 is a view of a sub-branching pattern of channels leading to the communicating tube.

The distribution and maintenance of negative pressure within the chamber device and at all points on the wound may be enhanced by providing defined channel spaces as pathways among the raised engineered structures for the distribution of negative pressure. However, defined channel spaces are not required for providing fluid pathways within the treatment space. FIG. 11 is an overview of a portion of the chamber wall, showing structures 47 arranged in two parallel lines to form channel 49. FIG. 12 shows a channel 49 formed by two parallel lines of raised domed structures 48. Such channels can be configured in various patterns, such as radial, circular, concentric, or branching. FIGS. 13-16 show overviews of patterns of channels 49 leading from tube 32 along the interior surface of chamber 22 facing treatment space 24. For each pattern, the channel 49 defines a space that opens directly to the treatment space 24. The space preferably opens to the treatment space 24 over the entire length of the channel 49.

Figure 17:
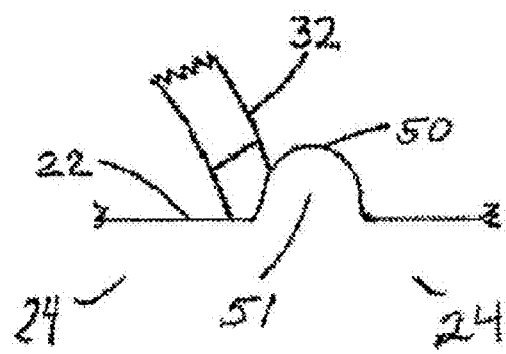
FIG. 17 is a side sectional view of a fold in the chamber wall.
Figure 18A:
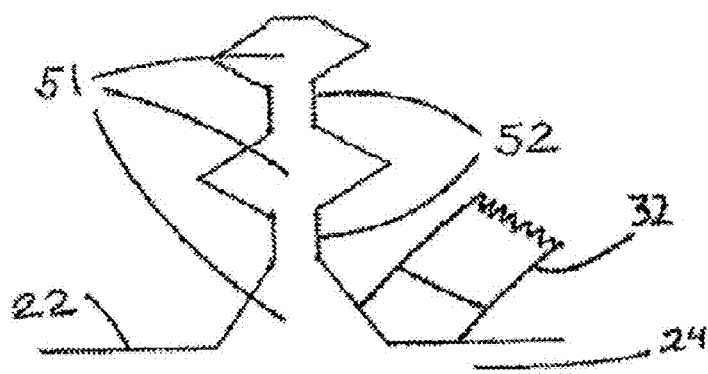
FIG. 18a is a side sectional view of a fold in the chamber wall, with structures engineered on and into the inner surface of the fold, which structures maintain continuous open space within the fold.
Figure 18B:
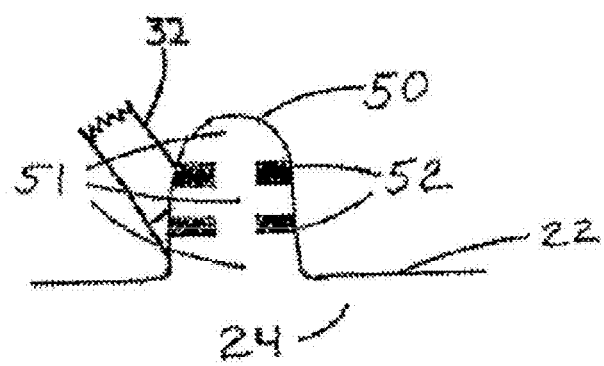
FIG. 18b is a side sectional view of the fold in the chamber wall of FIG. 17 with structures engineered on the inner surface of the fold.

The distribution and maintenance of negative pressure within the chamber device and at all points on the wound can also be enhanced by the use of folds in the chamber wall to create additional channel space for the distribution of negative pressure. When negative pressure is established within the chamber, the material will tend to fold along the pre-formed location. FIG. 17 shows a channel 50 formed in a fold of the chamber wall. The channel 50 defines a space that opens directly to the treatment space 24. The space preferably opens to the treatment space 24 over the entire length of the channel 50. In order to increase the amount of channel space within such fold, the walls of the fold can be configured with structures that prevent the collapse of such space, and ensure continuous open space for the distribution and maintenance of negative pressure, and the passage of liquid, gas, and other material. As an alternative, FIG. 18a shows engineered structures 52 that prevent the total collapse of the fold, and ensure continuous channel space 51. All channel spaces created on the interior surface of the chamber wall or by means of folds function as means to increase the effectiveness of distributing and maintaining negative pressure within the chamber, and also as means to enhance the effectiveness of removing gas, liquid, wound fluid, debris, and other materials from the chamber treatment space. As another alternative, FIG. 18b shows an embodiment similar to the embodiment shown in FIG. 17 with the addition of engineered raised structures 52 on opposite sides of the fold. The engineered structures 52 are provided so that the fold will not collapse to the point where all of its interior surfaces form a tight seal against the movement of negative pressure. However, some of the interior surfaces, such as those adjacent to the fold, preferably contact the wound to provide stimulation as discussed above. The folds described in the previous embodiments are preferably formed at certain defined areas by molding or embossing the surfaces of the chamber 22.

FIG. 19 shows a wound chamber device 120 for delivering negative pressure and therapeutic substances in the form of a tube that can be placed over a limb. The wound chamber device 120 is generally cylindrical and includes an open end and a closed end, though the chamber may have other shapes to accommodate other body parts, and may for example, be suitable for fitting over the head. The open end is preferably sealed with a cuff or collar (not shown), and the open end may include adhesive on the interior surface. The wound chamber device 120 includes engineered structures 40 and channels 49 on the interior surface of the chamber wall.

Figure 20:
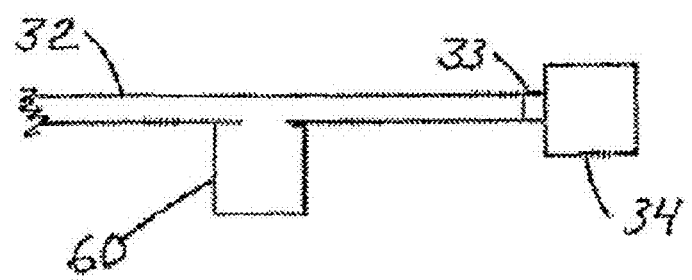
FIG. 20 is a sectional view of the device in FIG. 1 showing a fluid collector placed before the suction source.

As shown in FIG. 20, a fluid collector 60 may be positioned on the tube 32 between the chamber 22 and the suction device 34. The collector 60 is intended to receive fluid extracted from the chamber space 24 and debris or material from the wound and store such materials for eventual disposal. The collector 60 may be detachable from the tube 32, in order to replace a full collector with an empty collector.

Suction for the wound treatment device is provided by a suction device 34, which may be a pump that is connected and disconnected to the chamber device by appropriate connectors to provide sub-atmospheric pressure. Although the wound chamber can be used with a motor driven pump, it is also effective with a hand-powered device actuated by the caregiver or patient. The hand-powered device may be a squeeze bulb that provides suction by means of the energy stored in the material of its construction. Alternatively, the suction device may be powered by springs that are compressed by the user. The springs can be selected to produce the clinically desired level of negative pressure. The amount of suction provided by these suction devices is therefore dependent on the level of force generated by squeezed material or the springs. Unlike a motor driven suction pump, the hand powered device preferably cannot produce a high level of suction that may cause an adverse effect to wound healing.

Figure 21:
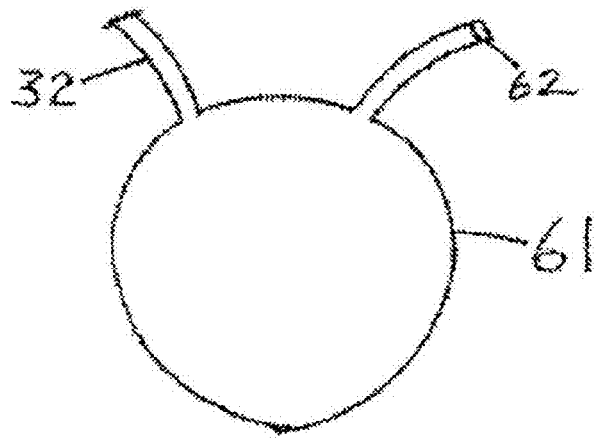
FIG. 21 is a sectional view of a suction device in the form of a squeeze bulb of deformable material.

Referring to FIG. 21, a suction device 61 in the form of a bulb constructed of a deformable material that stores the energy of deformation may be used. The tube 32 communicates with the interior of the suction device 61. A one-way exhaust valve 62 also communicates with the interior of the suction device 61. When the user squeezes the suction device 61, air within the device is expelled through the exhaust valve 62. A portion of the energy used to deform the suction device 61 is stored in the material of which it is constructed, thus maintaining suction within the device, as well as within the tube 32 and the chamber space 24. The bulb is selected and engineered to maintain a constant force and to maintain the clinically desired level of negative pressure within chamber space 24. Fluid from the wound 30 can flow through the tube 32 into the suction device 61 where it can be stored prior to disposal. Once the suction device is full of fluid, the production of negative pressure ceases. The fluid capacity of the suction device thus operates as a safety shut-off mechanism without the need for electronic sensors and controls.

Figure 22:
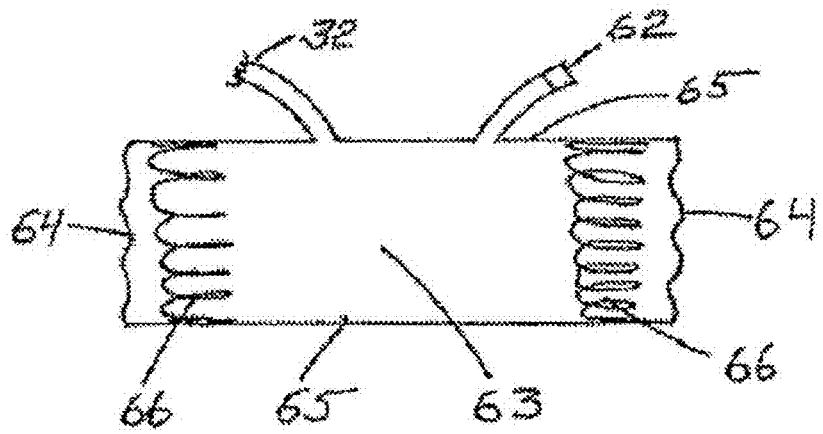
FIG. 22 is a sectional view of a suction device in the form of a flexible chamber containing one or more compression springs.

FIG. 22 shows an alternative suction device 63, consisting of flexible sides 64 and rigid sides 65. Compression springs 66 are located within suction device 63. The tube 32 and the exhaust valve 62 both communicate with the interior of the suction device 63. When the user squeezes the rigid sides 65 towards one another, the springs 66 are compressed and air within the device is expelled through a one-way exhaust valve 62 thus maintaining suction within the device, as well as within the tube 32 and the chamber space 24. The springs 66 are selected and engineered to maintain a constant force against rigid sides 65, and to maintain the clinically desired level of negative pressure within chamber space 24. Fluid from the wound 30 can flow through the tube 32 into the suction device 63 where it can be stored prior to disposal of the entire device 63. This suction device will also cease operating when it is filled with fluid.

Figure 23:
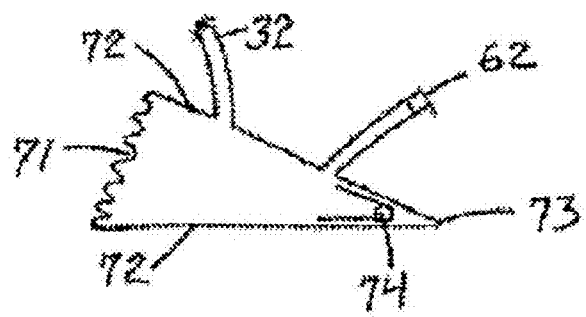
FIG. 23 is a sectional view of a suction device in the form of a wedge-shaped chamber containing one or more torsional springs.
Figure 24:
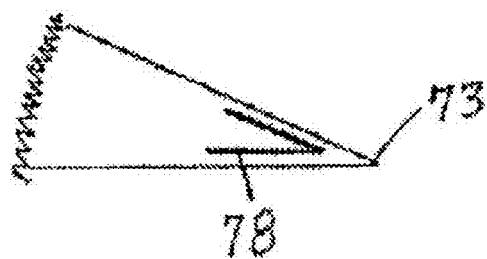
FIG. 24 is a sectional view of the device in FIG. 23 containing a flat spring.

FIG. 23 shows an alternative suction device 70, consisting of rigid sides 72, joined by hinge 73, and flexible side 71. A torsional spring 74 is attached to either the interior or the exterior of rigid sides 72. The tube 32 and the exhaust valve 62 both communicate with the interior of the suction device 70. When the user squeezes the rigid sides 72 towards one another, the spring 74 is compressed and air within the device is expelled through a one-way exhaust valve 62, thus maintaining negative pressure within the device, as well as within the tube 32 and the chamber space 24. The spring 74 is selected and made to maintain a force against rigid sides 72 to maintain the clinically desired level of negative pressure within chamber space 24. Fluid from the wound 30 can flow through the tube 32 into the suction device 70 where it can be stored prior to disposal of the entire device. FIG. 24 shows the device of FIG. 27 where the torsional spring 74 has been replaced by a flat spring 78.

For the previous suction devices, once suction has been established, fluid may flow from the wound to the suction device, where it may be collected and stored for eventual disposal. Alternatively, a separate fluid collector, such as the fluid collector 60 in FIG. 20, can be positioned between the chamber and the suction device. Once the suction device has expanded to its original shape, suction ceases. The suction device will not continue to operate, and can be disconnected and disposed of. If treatment is to be continued, a new suction device can be connected and activated.

Figure 25:
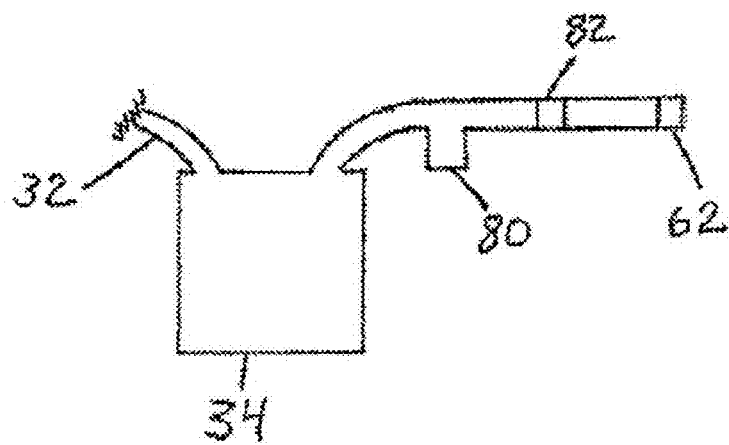
FIG. 25 is a sectional view of a suction device with a trap and filter incorporated into the exhaust port.

FIG. 25 is a sectional view of a trap 80 and a filter 82 interposed between the suction device 34 and the exhaust valve 62 for the purpose of preventing the expulsion of liquids or aerosols from the suction device.

The present disclosure can be engineered to operate at various levels of negative pressure, in accordance with clinical procedures. Traditional negative pressure wound healing devices can apply a negative pressure of between −0.5 and −2 psi, or about −750 mm Hg to about −125 mm Hg. The device of the present disclosure operates efficiently in this range. The chamber material conforms to the shape of the wound, and the embossed projections maintain their shape and functionality. However, the chamber can be engineered to operate at higher levels of negative pressure. The device of the present disclosure may also work efficiently at lesser negative pressures of for example from about −125 mm Hg to about −10 mm Hg. The application of less negative pressure may reduce pain and other complications. In addition, if a hand-powered suction device is used, the operating pressure of the device may be higher than the commonly accepted range; that is, the device may operate at a pressure close to 0 psi before suction ceases.

In accordance with one or more embodiments, a negative pressure wound therapy device may be vacuum-assisted to stimulate blood flow and new blood vessel growth, biomechanically stimulate cells to encourage division and proliferation, and to remove factors that might inhibit healing such as bacteria. Depending on the stage of treatment, connecting tubes can plug into different devices to apply negative pressure, drain a wound, and deliver therapeutic agents.

The present disclosure eliminates many of the drawbacks to existing negative pressure wound therapy systems. For example, the device of the present disclosure is preferably simplified and lightweight, and allows visual inspection of the wound. In some embodiments of the disclosure, the patient is not restricted to a source of electricity or a battery pack. The system can be worn with ease, so that the patient's mobility is not otherwise compromised. In addition, the wound interface appliance can be applied quickly without the need for custom fitting and construction. The device preferably does not leak due to the smooth adhesive base, eliminating the need for constant suction from an electric pump with sophisticated controls and safety measure. There is no interface material such as a porous wound insert that can potentially cause tissue in-growth and harbor infectious material. Instead, the inner surfaces of the chamber are generally non-porous and non-adherent to prevent any interaction with the wound tissue. Further still, the suction pump preferably has built-in safety limitations on force of suction, duration of operation, and overfilling of the collector for wound fluid. The engineered surface may stimulate the wound and create an efficient pathway for the distribution of negative pressure. The wound treatment chamber may be customized for use on any body part including limbs, as well as the head, face and/or neck. The devices and methods disclosed herein may be used in conjunction with conventional wound debridement and grafting techniques without any contraindications. The devices and methods may facilitate the fixation and protection of skin grafts and micrografts. The devices and methods may be superior to conventional approaches to administering negative pressure in terms of at least granulation tissue formation.

The function and advantage of these and other embodiments of the materials and methods disclosed herein will be more fully understood from the examples below. The following examples are intended to illustrate the benefits of the disclosed materials and methods, but do not exemplify the full scope thereof.

EXAMPLE 1

The effectiveness of the raised structures in distributing and maintaining negative pressure within the chamber and across the wound surface was demonstrated in a test model. A wound was created in a sample of animal cadaver tissue. A pressure sensor was installed in the tissue at the center of the wound. A wound chamber device with raised engineered structures on the interior chamber wall was sealed to the skin around the wound. A tube from the chamber device was connected to a source of suction capable of delivering a range of negative pressure. The amount of negative pressure measured at the suction source was compared to the measurement at the center of the wound, in order to determine the effectiveness of the device with respect to the distribution of negative pressure to the wound. The following values were obtained:

| Pressure at Source (mmHg) | Pressure in Wound (mmHg) |
| --- | --- |
| −80 | −65 (81.25% efficiency) |
| −100 | −86 (86.00% efficiency) |
| −120 | −100 (83.33% efficiency) |

The raised structures were observed to maintain their shape with no deformation, thereby preserving their functionality.

EXAMPLE 2

A patient with a full-thickness skin wound was treated with a wound chamber negative pressure device connected to a hand-powered suction pump. The interior surface of the chamber contained embossed raised structures. The area around the wound was treated with normal skin disinfectants. The backing from the adhesive base of the chamber was removed, and the chamber was sealed to the normal skin around the wound. The tube was connected to a modified squeeze bulb with an inlet port for fluid, and an exhaust port through which air can be expelled from the bulb. By squeezing the bulb down to its flattest configuration, a negative pressure of 2 pounds per square inch was established and maintained within the chamber. After the first twenty-four hours of treatment, the squeeze bulb had expanded to approximately half of its normal size. The bulb was compressed again to its fully flattened configuration. The bulb remained in such configuration for an additional twelve hours, at which point the chamber was removed. The wound showed healthy granulation tissue and progressed to heal rapidly and with minimal scarring. The device produced no adverse effects on the wound or the surrounding skin.

PROPHETIC EXAMPLE

Aspects of the present disclosure may be illustrated by the following prophetic example addressing injuries commonly resulting from military combat.

A patient was presented with partial and full thickness burns to the head, face, and neck. After evaluation, the wounds were thoroughly cleaned and dead tissue was removed. The patient's mouth and nose were closed with sutures. The patient was fitted with a tracheostomy tube and a gastrostomy tube. Protective lenses were inserted into the patient's eyes. A negative pressure device described herein having an oversized transparent chamber with internally embossed surface structures was applied over the patient's head and neck and sealed proximate the collar bone, above the tracheostomy and gastrostomy tubes.

The wound was treated according to the following regimen: in the first 24 hours, pain medication and chemical debriding agents were applied to the wounds by introducing the agents into the wound chamber, followed by high concentrations of anti-inflammatories, antibiotics, and anti-microbials to inhibit biofilm formation. The wounds were then chemically debrided a second time.

Negative pressure therapy was then applied for a time sufficient to prepare the wounds for skin grafts, for example, about 48 to 72 hours. During negative pressure therapy, the wounds were monitored by visual inspection through the transparent material of the chamber and by sampling the wound fluid for detection of bacteria. The negative pressure device was then removed and the wounds were treated with skin micrografts. The wounds were again covered by a new negative pressure chamber and therapeutic agents and negative pressure therapy were applied. The chamber helped maintain the skin grafts in place and the negative pressure therapy device stimulated cell and blood vessel growth to facilitate integration of the skin graft. Therapeutic agents were also applied as necessary to achieve optimal healing. The negative pressure chamber was replaced periodically, for example weekly or biweekly. The result was healed wounds with minimal scarring. Dedicated scar treatment followed to complete recovery.

It is to be appreciated that embodiments of the methods, devices, and apparatuses discussed herein are not limited in application to the details of construction and the arrangement of components set forth in the above description or illustrated in the accompanying drawings. The methods, devices, and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present devices and methods or their components to any one positional or spatial orientation.

Having described above several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

What is claimed is:

1. A method of treating a patient having a facial wound, comprising:
   debriding the facial wound;
   fitting a wound treatment device over a head of the patient, the wound treatment device comprising:
      a chamber configured to enclose a head and neck region of the patient, the chamber being made of an impermeable material that is sufficiently thin to conform to the head and neck of the patient, the chamber having a sealing portion at a base and an interior surface defining an isolated treatment space;
      a plurality of embossed structures on the interior surface of the chamber, the structures being configured to directly contact the facial wound and to create pathways for distributing negative pressure between the interior surface of the chamber and the facial wound; and
      at least one tube connected to the chamber and in fluid communication with the isolated treatment space so as to enable at least one of applying negative pressure to the isolated treatment space and applying a therapeutic agent to the facial wound;
   applying at least one therapeutic agent to the facial wound via the device; and
   applying negative pressure wound therapy to the isolated treatment space of the device for a sufficient duration to effect healing of the facial wound.

2. The method of claim 1, further comprising one or more of: surgically or non-surgically closing a mouth and a nose of the patient; applying a protective shield over an eye of the patient; and applying a tracheostomy tube and a gastrostomy tube to the patient.

3. The method of claim 1, wherein the plurality of embossed structures have a height of about 0.1 mm to about 5 mm.

4. The method of claim 3, wherein the plurality of embossed structures are positioned at a distance of about 0.2 mm to about 10 mm apart from one another.

5. The method of claim 1, wherein the plurality of embossed structures is positioned in a uniform pattern on the interior surface of the chamber.

6. The method of claim 5, wherein each embossed structure has a shape selected from the group consisting of: a cone, a pyramid, a pentagon, a hexagon, a half sphere, a dome, a rod, an elongated ridge with round sides, and an elongated ridge with square sides.

7. The method of claim 1, wherein the plurality of embossed structures intrudes into the isolated treatment space in a direction generally perpendicular to the interior surface of the chamber.

8. The method of claim 1, wherein the device is configured to treat the facial wound for a prolonged duration of a healing process.

9. The method of claim 1, wherein the chamber is formed from a single sheet of material.

10. The method of claim 1, wherein the at least one tube is further configured to remove wound fluid from the isolated treatment space.

11. The method of claim 1, wherein the plurality of embossed structures structure are semi-rigid.

12. The method of claim 1, wherein the sealing portion includes a first surface having an adhesive.

13. The method of claim 1, wherein the device further comprises at least one of: a fluid trap, an exhaust port, and a suction device.

14. The method of claim 1, wherein the device further comprises a manual pump in fluid communication with the isolated treatment space to apply the negative pressure wound therapy.

15. The method of claim 1, wherein the at least one therapeutic agent comprises an agent selected from the group consisting of: antimicrobials, antibiotics, antifungals, and analgesics.

16. The method of claim 1, wherein the chamber does not comprise a porous insert.

17. The method of claim 1, wherein the plurality of embossed structures covers at least 95 percent of the interior surface of the chamber.

* * * * *